PREPARATION OF N-(PHOSPHONOACETYL)-L-ASPARTIC ACID

The invention described herein was made in the course of work under a grant or award from the Department of Health, Education and Welfare.

BACKGROUND AND SUMMARY OF THE INVENTION

The present invention relates to improved methods for preparation of N-(phosphonoacetyl)-L-aspartic acid, also known as PALA, in the form of the tetrasodium or disodium salt. More particularly, the present invention is concerned with a method for the large scale preparation of the tetrasodium salt and the disodium salt of N-(phosphonoacetyl)-L-aspartic acid.

The compound, N-(phosphonoacetyl)-L-aspartic acid (PALA), was first prepared as a rationally designed transition state analogue inhibitor of aspartate transcarbamylase, as described by Stark et al., *J. Biol. Chem.*, 246, 6599 (1971). Subsequent publications have presented an improved synthetic scheme for gram amounts of PALA, and have demonstrated inhibition of pyrimidine nucleotide biosynthesis in vitro, as discussed by Stark et al., *J. Biol. Chem.*, 249, 6945 (1974), as well as in vivo, as discussed by Yoshida et al., *J. Biol. Chem.*, 249, 6951 (1974). PALA has been shown to be active against the B16, Lewis Lung, and P388 tumor systems, as indicated in the NCI screening program, Selected Agents List, Drug Evaluation Branch, DR and DP, Data through August 31, 1976, p. 143.

While the synthesis of PALA is straightforward, the preparation of the tetrasodium salt or the disodium salt in kilogram quantities has proven to be a major problem. The method of the present invention is particularly well suited for the production of such quantities. In copending U.S. Patent Application Ser. No. 851,382, filed Nov. 14, 1977, commonly assigned, there is described a method for the preparation of the tetrasodium and disodium salts of PALA, and this application is incorporated by reference herein.

DESCRIPTION OF THE PREFERRED EMBODIMENTS

The method for the preparation of the disodium salt of PALA in accordance with the present invention is summarized in Outline I. As can be seen in Outline I, the present method includes the initial preparation of phosphonoacetyl chloride. Phosphonoacetyl chloride was originally prepared in thionyl chloride at 60° C. The excess thionyl chloride was removed by evaporation in vacuo, then the oily residue was dissolved in dioxane. This solution was then added to dibenzyl aspartate in dioxane containing triethylamine at ~15°. The insoluble triethylamine hydrochloride was filtered off, the dioxane was removed at reduced pressure, then the residue was dissolved in benzene. This was later changed to methylene chloride because of the OSHA restrictions on the use of benzene.

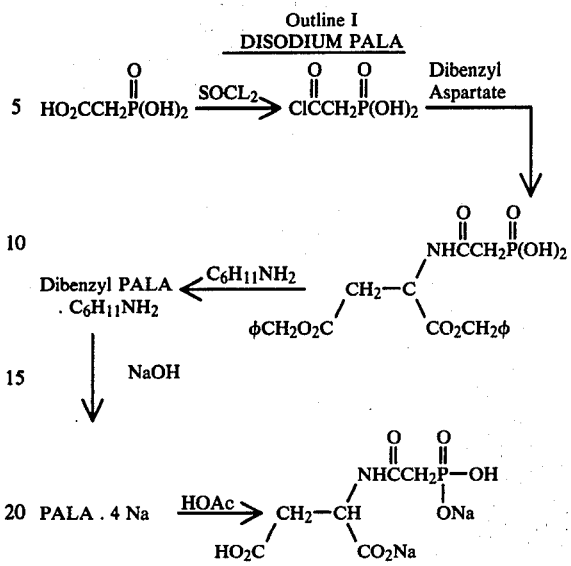

The organic solution was then washed several times with water in order to remove unreacted acid chloride.

This procedure was acceptable on a small scale, however, many changes were necessary in order to have a suitable production process.

Removal of the excess thionyl chloride in the preparation of phosphonoacetyl chloride posed a major problem for scale-up. The reaction was therefore attempted with one equivalent of thionyl chloride in dioxane. It was observed that, under completely anhydrous conditions, the reaction with dibenzyl aspartate gave ~70–80% of an unknown material. With the assumption that over chlorination was occurring, it seemed likely that, under the appropriate conditions, the P-Cl bond could be hydrolyzed by the addition of water. This proved to be the case. The chlorination has been successfully carried out in dioxane using from about 2.0 to 2.1 equivalents of thionyl chloride followed by the addition of from about 1.0 to 1.2 equivalents of water. The dibenzyl PALA obtained in this manner still contains a small amount of the unknown impurity. However, this can be eliminated through a salt formation or through formation of the cyclohexylammonium salt.

Other necessary modifications were made in order to improve the scale-up capability of the process. Dioxane, because of its flammable and toxic properties, was unattractive for large scale runs. A suitable substitute for the chlorination reaction proved to be a mixture of glyme (1,2-dimethoxyethane) and methylene chloride in a volume ratio of 40:60. This solvent mixture is less toxic than dioxane and was determined to be nonflammable.

The present method employs, as a key step in the sequence, the use of dibenzyl aspartate. Reaction of the diester with phosphonoacetyl chloride gives the water insoluble dibenzyl PALA. Preparation of this intermediate allows for the convenient removal of unreacted, water soluble acid chloride. Hydrolysis of dibenzyl PALA, purification of the reaction mixture by a batch ion exchange process, and adjusting an aqueous solution of the free acid to pH 9.2 gives the desired tetrasodium salt.

The synthesized compound appeared to be free of significant organic contamination as determined by NMR, O.R., and TLC, and was reported to be active in the expected tumor systems. Analysis of the material,

United States Patent [19]

Parsons et al.

[11] 4,154,759

[45] May 15, 1979

[54] PREPARATION OF N-(PHOSPHONOACETYL)-L-ASPARTIC ACID

[76] Inventors: Jack L. Parsons, 800 Maple Rd., East Aurora, N.Y. 14050; Henryk Dubicki, 52 Steinfeldt Rd., Lancaster, N.Y. 14086

[21] Appl. No.: 932,506

[22] Filed: Aug. 10, 1978

[51] Int. Cl.² .............................................. C07F 9/38
[52] U.S. Cl. ............................................... 260/502.5
[58] Field of Search ................................... 260/502.5

[56] References Cited

U.S. PATENT DOCUMENTS

| 3,417,098 | 12/1968 | Anatol | 260/502.5 |
| 4,016,148 | 4/1977 | Ratcliffe et al. | 260/502.5 |

FOREIGN PATENT DOCUMENTS 1488426  6/1967  France ................................. 260/502.5

OTHER PUBLICATIONS

Vogel, "Practical Organic Chemistry" (1948), pp. 122–131.

*Primary Examiner*—Joseph E. Evans
*Attorney, Agent, or Firm*—Holman & Stern

[57] ABSTRACT

Improved methods for preparation of the tetrasodium and disodium salts of N-(phosphonoacetyl)-L-aspartic acid (PALA) are disclosed. The present methods are well suited for preparation of these products in large amounts. A particular aspect of these methods includes a water-ethanol washing procedure for reducing impurities, including acetic acid, sodium acetate and ethanol, to an acceptable level.

1 Claim, No Drawings

In a similar fashion, after esterification was completed, the reactor must be discharged at 80°–90° C.

Process control methods were devised based on thin layer chromatographic examination of the reaction mixture. The optimum time for esterification was determined by TLC. Moreover, TLC markers of possible side-products were obtained to relieve concern as to any tangential reactions. For example, the possible reaction of the toluenesulfonic acid with the amine of aspartic acid leading to the sulfonamide was shown not to occur under the conditions of the desired esterification.

By retaining the product as the tosylate salt, the reactor could be discharged directly into an optimum volume of acetone. The acetone was cooled with dry-ice. The pure ester precipitated immediately and only needed to be washed with acetone before being dried. The product was of sufficient quality that no impurities were carried into subsequent steps in the production of PALA. Dibenzyl aspartate quality control included the established characteristics in IR, NMR, optical rotation, and elemental analyses.

The development of the present process is illustrated by the results of development runs which are summarized in Table I.

Table I

| Reactor Size | Amount Aspartic Acid | Yield (%) | Amount of Ester |
|---|---|---|---|
| 250 ml. | 13 g. | 60–75 | — |
| 3 liter | 133 g. | 65–75 | — |
| 12 liter | 532 g. | 73 | 1,420 g. |
| 76 liter (20 gallon) | 3,200 g. | 64 | 7,400 g. |
| 76 liter (20 gallon) | 3,200 g. | 72 | 8,400 g. |
| 380 liter (100 gallon) | 16,000 g. | 64 | 37,500 g. |
| 380 liter (100 gallon) | 16,000 g. | 68 | 39,000 g. |

Good yield retention has been obtained on scale-up. The purity is equal to or greater than 99% from the process with a present yield of about 65%. The production per unit time is only limited by the size of the reactor. Moreover, the process information is developed to a level for easy transfer to larger equipment.

The preparation of disodium PALA, as outlined in Outline III, results in a product contaminated with sodium aspartate, sodium acetate, unknown phosphorus—containing materials and the solvents acetic acid and ethanol.

The dibenzyl PALA used for hydrolysis contains unreacted dibenzyl aspartate which leads to sodium aspartate under the reaction conditions. The sodium acetate arises from the partial neutralization of the tetrasodium PALA and from the excess sodium hydroxide used in the hydrolysis.

Two impurities which require elimination are acetic acid and sodium acetate. On a 500 g. scale, all of the sodium acetate and most of the acetic acid can be removed by extensive washing with ethanol. On a larger scale, this did not prove to be the case. The sodium acetate could be removed, however, by a second precipitation from acetic acid.

On a 10 g. run, the ethanol and acetic acid were completely eliminated by freeze-drying; however, this method was not operable when scaled up to 2 kg. This is an example of one of the vagaries of scale-up technology. This problem was solved by precipitating the crude disodium PALA twice from water using ethanol. This method removed all of the acetic acid and sodium acetate. The second precipitation is a dropwise addition of an aqueous solution of PALA to the vortex of vigorously stirred ethanol. The disodium salt precipitates as a granular solid. This method is suitable for quantities up to about 2 kg. For 25 kg. of the target material, this step alone would require almost 400 gallons of ethanol; for 60 kg., nearly 1000 gallons of ethanol would be needed.

It has now been determined that washing the PALA which is precipitated from acetic acid with an appropriate water-ethanol solution can completely remove the acetic acid and sodium acetate. This purification procedure requires that 92±1% by volume aqueous ethanol be employed. If more water is present, the material does not remain in solid form. If less water is used, the process is inoperative. The temperature at which this purification procedure is carried out is also critical. The optimum temperature for conducting the washing procedure with the aqueous ethanol is from about 26° to about 28° C. At temperatures above 30° C., the compound turns from a solid to an oil. At temperatures below 25° C., the procedure has been found to be ineffective. Thus the relatively narrow limits of water concentration and temperature must be employed, otherwise the impurities cannot be removed from the product.

This practical leaching procedure reduces the volume of ethanol by at least 50% and results in the saving of considerable man-hours. An additional problem of ethanol solvation had existed. Ethanol concentration in the end product was at a 6–9% level. The leaching process causes a substitution of solvates, i.e., water for ethanol, thus reducing the ethanol to an acceptable 1 to 2%.

Thus there is provided a process that reduces acetic acid, sodium acetate, and ethanol impurities to acceptable levels. Two major contaminants must still be controlled. These are aspartic acid and the unidentified phosphorus compounds.

The aspartic acid can be detected on TLC by spraying with ninhydrin. PALA is visualized on the chromatogram using a molybdate spray and appears as one spot in all of the solvent systems employed. However, a number of phosphorus impurities, totaling 6% could be detected using $P^{31}$ NMR. It was believed that these phosphorus impurities did not originate during either the hydrolysis or neutralization steps. As they were not present in the starting phosphonoacetic acid, they had to be formed during the preparation of the dibenzyl PALA. This was confirmed by $P^{31}$ NMR which contained peaks other than that attributed to dibenzyl PALA.

Outline V
PURIFICATION OF DIBENZYL PALA

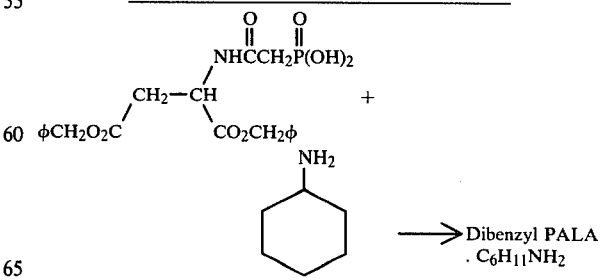

To prevent the formation of these impurities would require more extensive research and possible routing alterations. The decision was made to minimize their formation, then remove the phosphorus contamination from the dibenzyl PALA. This was carried out by the method as shown in schematic in Outline V.

Upon preparation of the cyclohexylammonium salt of dibenzyl PALA, the dibenzyl PALA liberated from this purified salt was analyzed and found to give 1 peak in the $P^{31}$ NMR. In addition, both the liberated dibenzyl PALA and the amine salt were subjected to the hydrolysis and partial neutralization steps. The $P^{31}$ spectra of the resultant disodium PALA samples confirmed that the phosphorus impurities could be eliminated by this salt formation.

In addition to eliminating the phosphorus contaminants, the amine salt formation also removes the unreacted dibenzyl aspartate. This results in a final product free of aspartic acid contamination.

Scale-up development for the preparation of the pure salt has overcome some potentially serious manipulative problems. The salt is prepared by adding from about 0.9 to about 1.0 equivalent of cyclohexylamine to an acetone solution of dibenzyl PALA. The product is insoluble in acetone whereas a large percentage of the impurities remain in solution. It was found that the reaction must be run under anhydrous conditions with gentle mixing of the reactants, otherwise a gelatinous product will result. On a multi-kilogram scale, this material would be nearly impossible to isolate. The purity of the product is upgraded to an acceptable level by recrystallization from absolute methanol.

Difficulties are encountered in the use of dioxane for the preparation of dibenzyl PALA. As mentioned, triethylamine hydrochloride is an insoluble by-product of the reaction, and large volumes of solvent are required in order to maintain sufficient stirring. In addition, the reaction is exothermic, and the use of dioxane limits the extent of cooling to ~12°, which is the temperature at which dioxane freezes.

The solvent substituted for dioxane in this reaction was methylene chloride. This solvent offers the following advantages: (a) It is nonflammable; (b) It allows for a lower cooling temperature; (c) The volume of solvent is reduced in half; (d) The removal of triethylamine hydrochloride by filtration is eliminated since it is soluble in the reaction mixture; and (e) The evaporation of the solvent prior to work-up is no longer necessary.

The work-up involves aqueous washes of the methylene chloride solution in order to remove unreacted acid chloride and triethylamine hydrochloride. A considerable emulsion problem was encountered during this washing procedure. This difficulty has been eliminated by substituting diluted hydrochloric acid for the water.

Additional process improvements include the fact that the cyclohexylammonium salt is hydrolyzed directly to the tetrasodium PALA. This eliminates the extra manipulation of releasing the dibenzyl PALA from the amine salt prior to hydrolysis.

Another improvement is the azeotropic removal of water from the hygroscopic dibenzyl PALA with chloroform prior to salt formation. This results in a more crystalline salt and ultimately in a higher yield.

A final point is that the volume of water required for the hydrolysis has been reduced by 63% over that used in the initial synthetic work. This, of course, allows for larger scale runs to be made using the same size equipment. At the bench scale, using as a maximum 50 l. flasks, this procedure has been used to prepare disodium PALA in ~2 kg. lots. Incorporating all of the described modifications, a run using 50 and 100 gallon Pfaudlers has been successfully carried out. At full scale, ~15 kg. of the target material can be produced per run using this size equipment. The process, as currently developed, is limited only by the size of the equipment.

By the present method, the purity of the desired material has been upgraded to a satisfactory IND level. This was accomplished by (1) a convenient washing procedure which eliminates the acetic acid and sodium acetate and reduces the ethanol content; and (2) by preparing the cyclohexylammonium salt of dibenzyl PALA which removes the aspartic acid and phosphorus-containing contaminants. In addition, the procedure has been optimized for ease of scale-up, and the problems of process manipulations have been solved.

Example 1 provides one sequence of steps in preparing the disodium salt of PALA while Example 2 provides a separate sequence of steps for the preparation of the disodium salt of PALA.

EXAMPLE 1

Phosphonoacetyl chloride

A 50-gallon Pfaudler reactor was purged with nitrogen to a measured oxygen content of <3%, then charged with methylene chloride (24 l.), 1,2-dimethoxyethane (16 l.), N,N-dimethylformamide (1.76 l.), and phosphonoacetic acid (16.0 kg.; 114 moles). The stirred mixture was cooled to 5°, then thionyl chloride (28.56 kg.; 240.0 moles) was added in a thin stream during 3 hours. The temperature of the reaction mixture was maintained between 10° and 15° during the addition. The resulting solution was heated at 30° for 3 hours, then the temperature was increased to 43° during the next hour. Additional methylene chloride (20.0 l.) was added, then the stirred solution was cooled (0°) and stored for 12 hours at 0°-3°. To this solution was added water (2.44 l.; 137 moles), dissolved in 1,2-dimethoxyethane (8.0 l.), in a thin stream over a period of 4 hours while maintaining the reaction temperature between 0° and 3°. After the addition was completed, the solution was stirred an additional 0.5 hour at 0°, then immediately used in the next reaction.

L-Aspartic acid, N-(phosphonoacetyl)-, dibenzyl ester

A 100-gallon Pfaudler reactor purged with nitrogen was charged in succession with methylene chloride (120 l.), L-aspartic acid, dibenzyl ester p-toluenesulfonate (40.75 kg.; 83.93 moles), and triethylamine (58.6 l.). The stirred solution was cooled to 5°, then the phosphonoacetyl chloride (114.3 moles) was added in a thin stream during 3 hours while the temperature was maintained between 10° and 18°. Additional triethylamine (6.0 l.) was added, and the mixture was stirred an additional 0.5 hour, then stored for 12 hours at room temperature. Methylene chloride (120 l.) was added, and the solution was washed in succession with 10% aqueous hydrochloric acid (2×114 l.), 5% aqueous hydrochloric acid (3×114 l.) and water (114 l.). The organic layer was dried over sodium sulfate (34.2 kg.) and magnesium sulfate (6.9 kg.) then concentrated in vacuo to 75 l. in a 100-gallon Pfaudler. Trace amounts of water were removed by co-distillation with chloroform (150 l. and 190 l.). Trace amounts of chloroform were removed by co-distillation with acetone (150 l.). The resulting thick oil was diluted with acetone (300 l.), then used immediately in the next reaction.

L-Aspartic acid, N-(phosphonoacetyl)-, dibenzyl ester, complexed with cyclohexylamine Cyclohexylamine (7478 g.; 75.54 moles) was added, in a thin stream, to a gently stirred solution of L-aspartic acid, N-(phosphonoacetyl)-, dibenzyl ester (II) (36.50 kg.; 83.93 moles) in acetone (300 l.) at 20° during 20 minutes. The resulting mixture was stored for 12 hours at 5°–10°, then the precipitate was collected and washed with acetone (70 l.). The material was resuspended in acetone (230 l.), stirred for 30 minutes, collected, washed with additional acetone (2×30 l.), then dried in vacuo (40°) to give 33.45 kg. (74.7%) of product. (33.2 kg.). This material was suspended in boiling methanol (527 l.). Celite (1.7 kg.) and cellulose (500 g.) were added, and the suspension was heated at reflux for 3 hours. Insolubles were removed by filtration (Celite). The clear filtrate was diluted with acetone (400 l.), and the resulting mixture was stored for 16 hours at 5°–10°. The precipitated solid was collected, washed with acetone (40 l.), then dried in vacuo (40°) to give 17.49 kg. (52.6% recovery) of purified product. The mother liquor was concentrated in vacuo, and an additional 7.31 kg. of material was obtained to give a total of 24.80 kg. (75% recovery) of purified product.

L-Aspartic acid, N-(phosphonoacetyl)-, tetrasodium salt

To a cold (2°), stirred solution of sodium hydroixde (97%) (7532 kg.; 182.7 moles) in distilled water (114 l.) was added L-aspartic acid, N-(phosphonoacetyl)-, dibenzyl ester, complexed with cyclohexylamine (23.8 kg.; 44.5 moles) during 30 minutes while maintaining the temperature of the mixture at 10°–15°. The mixture was stirred at 15° for 4 hours then stored at 10° for 16 hours. The aqueous solution was washed with methylene chloride (4×75 l.). Decolorizing carbon (700 g.) and Celite (1 kg.) were added to the aqueous solution. The mixture was stirred for 30 minutes then clarified by filtration. The filtrate was diluted with ethanol (410 l.) then stored at 10° for 8 hours. The supernatant alcohol layer was removed, and the heavy oil washed with additional ethanol (6.5 l.) then immediately used in the next reaction.

L-Aspartic acid, N-(phosphonoacetyl)-, disodium salt .1.3 H$_2$O.0.13 EtOH

Glacial acetic acid (70.0 l.) was added to the L-aspartic acid, N-(phosphonoacetyl)-, tetrasodium salt oil from the above reaction. The mixture was stirred at room temperature for 30 minutes, clarified by filtration, then ethanol (238 l.) was added to the stirred solution during 1.75 hours. The mixture was stirred an additional hour then stored at 10° for 20 hours. The resulting precipitate was collected then washed with ethanol (12.0 l.). This material was washed by resuspension with 92% ethanol - 8% water (60 gal.) at 27° for 15 hours in a 100-gallon Pfaudler reactor. The solid was collected then washed on the filter with absolute ethanol (4×1.5 gal.). The solid was washed a second time with 92% ethanol - 8% water (60 gal.) at 26° for 15 hours. The solid was collected, washed on the filter with absolute ethanol (5×2 gal.), then dried to constant weight in vacuo (first at room temperature, then at 40°) to give 12,154 g. (76%) of purified product. The melting point of this material is non-determinant.

Anal. Calc'd. for C$_6$H$_{7.7}$NO$_8$P . 2.3 Na . 1.3 H$_2$O . 0.13 EtOH

|  | C | H | N | P | Na |
|---|---|---|---|---|---|
|  | 22.44 | 3.33 | 4.18 | 9.24 | 15.78 |
| Found | 22.69 | 3.43 | 4.20 | 9.27 | 15.81 |

Sodium analysis indicates a composition of
70% di-NaPALA
30% tri-NaPALA
Based on empirical formula and spectral data,
% H$_2$O = 7.0%
% EtOH = 1.8%
Spectral Data
Infrared (Nujol): Major bands: 3400-3200, 2920, 2850, 1730-1690, 1650-1580, 1460, 1370, 1170-1140, 1070-1030, 910-870 cm$^{-1}$
Nuclear Magnetic Resonance (D$_2$O): δ 4.70 (HOD); 4.50 (t, 1, —CH—, J=6.0 Hz); 3.60 (q, 0.3, —CH$_2$— of ethanol, J=7.0 Hz); 3.00-2.50 (m, 4, methylene H); 1.15 (t, 0.4, —CH$_3$ of ethanol, J=7.0 Hz)

| Optical Rotation: | |
|---|---|
| Observed | Literature |
| [α]$^{23}_D$ + 14.56° (c, 0.206 in H$_2$O) | [α]$^{22}_D$ + 14.86° (c, 1.998 in H$_2$O) |

Chromatography:

Thin Layer Chromatography
(Cellulose, Quanta/Gram Q2F Glass Plates)

| Solvent System | R$_f$ Value |
|---|---|
| 1. Lithium chloride (0.6 M)-ethanol-ammonium hydroxide (5:5:1) | 0.47 |
| 2. Ethanol-water (2:3) | 0.78 |
| 3. Ethanol-ammonium hydroxide-water (6:1:3) | 0.22 (elongated) |
| 4. n-Butanol-acetic acid-water (5:2:3) | 0.30 (tailing) |

Detection: (a) Ninhydrin (b) Phospray
Quantity Spotted: 300 μg.
Results: The compound moves as one phospray positive spot in each of the solvent systems. No aspartic acid was observed on spraying with ninhydrin.

EXAMPLE 2

Phosphonoacetyl chloride

To a stirred mixture of phosphonoacetic acid (2000 g.; 14.28 moles), N,N-dimethylformamide (208.8 g.; 2.856 moles), and dioxane (7.15 l.) was added, dropwise, thionyl chloride (3568 g.; 29.99 moles) during 1.5 hours. The temperature was maintained below 30° during the addition. The resulting solution was heated at 45° for 2.5 hours then cooled to 5°. Water (283 ml.; 15.7 moles) dissolved in dioxane (2.5 l.) was then added, dropwise, over a period of 2 hours. The temperature was kept below 10° during the addition. This solution of acid chloride was stirred at 5°–10° for 40 minutes then used in the following reaction without further characterization. A second chlorination was carried out concurrently, under the same conditions, using identical quantities of reactants.

L-Aspartic acid, N-(phosphonoacetyl)-, dibenzyl ester

A stirred suspension of L-aspartic acid, dibenzyl ester p-toluenesulfonate (4625 g.; 9.525 moles) in dioxane (20.0 l.) was cooled to 15°, then triethylamine (4820 g.; 47.63 moles) was added, in a thin stream, during 1 hour. The resulting solution was stirred for 20 minutes, then the above solution of phosphonoacetyl chloride, prepared from 14.28 moles of the corresponding acid, was added, dropwise, over a period of 5 hours. The temperature was maintained below 20° during the addition. Additional triethylamine (1162 g.; 11.48 moles) was added and the reaction mixture was stirred for 1 hour. After standing for 8 hours at room temperature, the mixture was diluted with acetone (5.5 l.), stirred for 15 minutes, then the insolubles were collected on a filter and washed with dioxane (10.0 l.). A second reaction was carried out concurrently, under the same conditions, using identical amounts of materials. The filtrates from the two runs were combined and spin-evaporated in vacuo. The residue (orange, viscous oil) was dissolved in methylene chloride (110.0 l.), then the organic solution was gently washed with water (6×30.0 l.). After drying the solution over sodium sulfate (11.3 kg.) and magnesium sulfate (2.3 kg.), the insolubles were filtered off (Celite pad), and the filtrate was evaporated in vacuo to constant weight; yield of dibenzyl PALA, 7970 g. (96.1%). This yellow, viscous oil was suitable for further transformation.

L-Aspartic acid, N-(phosphonoacetyl)-, dibenzyl ester, complexed with cyclohexylamine Cyclohexylamine (1815 g.; 18.30 moles) was added, dropwise, to a cold (7°), stirred solution of L-aspartic acid N-(phosphonoacetyl)-, dibenzyl ester (7970 g.; 18.30 moles) in acetone (24.0 l.) during 1.25 hours. The temperature was maintained below 15° during the addition. The cooling bath was removed, and the resulting mixture was stirred for 1 hour. The mixture was stored at room temperature for 6 hours, then the precipitated solid was collected on a filter, washed with acetone (15.0 l), and dried; yield, 4932 g.; m.p., 176.5°–177.5°. This material was recrystallized from boiling methanol (35.0 l.) then dried to give 1663 g. of the purified salt; m.p., 178°–181°; literature m.p., 186°–188°. The mother liquor was concentrated in vacuo to a volume of 20.0 l. The solution was diluted with acetone (16.0 l.) and cooled (−10°) to give an additional 967 g. of product; m.p., 177°–180°. A third crop of material (429 g.) was obtained by evaporating the above methanol-acetone filtrate to near dryness and suspending the residue in acetone (5.0 l.); total amount of the purified amine salt suitable for further transformation, 3059 g. (62.0% recovery).

L-Aspartic acid, N-(phosphonoacetyl)-, tetrasodium salt

To a cold (5°), stirred solution of sodium hyroxide (1291 g.; 32.28 moles) in water (20.5 l.) was added, in portions, during 30 minutes, L-aspartic acid, N-(phosphonoacetyl)-, dibenzyl ester, complexed with cyclohexylamine (3059 g.; 5.378 moles if the amine salt has the same empirical formula as the analytically pure sample). The reaction mixture was stirred at 5°–15° for 3.5 hours, then extracted with methylene chloride (2×8.5 l.) and ether (1×8.5 l.). The aqueous solution was clarified by filtration, concentrated in vacuo (<35°; 3–5 mm. Hg) to a volume of 14.6 l., then diluted with ethanol (51.4 l.). The resulting mixture was stirred for 1 hour and stored at room temperature for 12 hours. The aqueous ethanol solution was removed giving crude product as a light yellow oil suitable for further transformation.

L-Aspartic acid, N-(phosphonoacetyl)-, disodium salt

Glacial acetic acid (8.0 l.) was added to the above precipitated oil [crude L-aspartic acid, N-(phosphonoacetyl)-, tetrasodium salt prepared from 3059 g. of the amine salt]. The mixture was stirred at room temperature for 30 minutes, then a gelatinous insoluble was filtered off. The clear, light yellow filtrate was diluted with ethanol (24.0 l.). The resulting mixture was stirred for 1.75 hours, then the precipitated material was collected on a filter. The solid was suspended in ethanol (14.5 l.), and the mixture was vigorously stirred for 1 hour. The product was collected on four filters then partially dried by spin-evaporation in vacuo (30°–45°; aspirator pressure than 3–5 mm. Hg). The lumpy material (2870 g.) was dissolved in water (5.25 l.), the solution was clarified by filtration, then the filtrate (~6.9 l. volume) was diluted with ethanol (21.0 l.). The resulting mixture was stirred for 30 minutes, then the precipitated oil was allowed to settle (1 hour). The aqueous ethanol solution was removed, and the oil was washed once with ethanol (4.3 l.). This material was dissolved in water (8.15 l), and the solution (9.8 l.) was divided into three portions (two of 4.0 l.; one of 1.8 l.). Each portion was added, during 13 hours, to the vortex of vigorously stirred ethanol (10×aqueous volume: 2×40.0 l.; 1×18.0 l.). After stirring the mixtures for 2 hours, the water-ethanol solutions were siphoned off, and the solid from the three precipitations was combined. The material was stirred for 30 minutes in ethanol (10.0 l.), collected on a filter, then dried to constant weight in vacuo at room temperature over phosphorus pentoxide. The dried product (1748.0 g.) was passed through a 150μ, stainless steel sieve and thoroughly blended to give (V) as a white powder.

Anal.
Calc'd. for $C_6H_{7.6}NO_8P \cdot 2.4\ Na \cdot 2\ H_2O \cdot 0.5\ C_2H_6O$

|  | C | H | N | P | Na |
|---|---|---|---|---|---|
|  | 22.91 | 4.01 | 3.82 | 8.44 | 15.04 |
| Found | 23.16 | 3.76 | 3.79 | 8.57 | 15.18 |

Sodium analysis indicates a composition of
60% di-Na PALA
40% tri-Na PALA
Based on the empirical formula,
% $H_2O$ = 9.8%
% EtOH = 6.3%

Spectral Data: Nuclear Magnetic Resonance ($D_2O$): δ 1.17 (t, 1.5, —$CH_2$ of ethanol); 2.74 (d, 2, —$CH_2$ α to —CH); 2.77 (d, 2, J=20 Hz, —$CH_2$ α to P); 3.63 (q, 1, —$CH_2$ of ethanol); 4.48 (t, 1, —CH)

Optical Rotation:

| Observed | Literature |
|---|---|
| $[\alpha]^{22.5}_D$ + 14.73 (c, 2.098 in water) | $[\alpha]^{22}_D$ + 14.86 (c, 1.998 in water) |

Chromatography:

Thin Layer Chromatography
(Cellulose, Quanta/Gram Q2F Glass Plates)

| Solvent System | $R_f$ Value |
|---|---|
| 1. Lithium chloride (0.6 M)-ethanol-ammonium hydroxide (5:5:1) | 0.52 |
| 2. Ethanol-water (2:3) | 0.72 |
| 3. Ethanol-ammonium hydroxide-water (6:1:3) | 0.16 (elongated) |
| 4. n-Butanol-acetic acid-water | 0.22 |

(5:2:3)  (tailing)

Detection: (a) Ninhydrin (b) Phospray
Results: The compound moves as one phospray positive spot in each of the solvent systems. No aspartic acid was observed on spraying with ninhydrin.

It is thought that the invention and many of its attendant advantages will be understood from the foregoing description, and it will be apparent that various changes may be made in the methods as described herein without departing from the spirit and scope of the invention or sacrificing its material advantages, the forms hereinbefore described being merely preferred embodiments thereof.

The embodiments of the invention in which an exclusive property or privilege is claimed are defined as follows:

1. In a method for the preparation of a sodium salt of N-(phosphonoacetyl)-L-aspartic acid by reacting L-aspartic acid, dibenzyl ester p-toluenesulfonate with triethylamine, followed by the addition of phosphonoacetyl chloride to produce the N-(phosphonoacetyl)-L-aspartic acid moiety in the form of the dibenzyl ester, wherein the carboxyl groups of the N-(phosphonoacetyl)-L-aspartic acid are esterified, adding cyclohexylamine under anhydrous conditions to produce the cyclohexylamine salt of said dibenzyl ester, reacting said cyclohexylamine salt with sodium hydroxide to produce L-aspartic acid, N-(phosphonoacetyl)-, tetrasodium salt, and reacting said tetrasodium salt with acetic acid to produce L-aspartic acid, N-(phosphonoacetyl)-, disodium salt, the improvement which comprises subjecting the obtained disodium salt to a water-ethanol washing procedure, employing 92±1% by volume aqueous ethanol, said washing procedure being carried out at a temperature of from about 26° to about 28° C., thereby reducing impurities, including acetic acid, sodium acetate and ethanol, to an acceptable level.

* * * * *